United States Patent [19]

Brandman et al.

[11] 4,217,363

[45] Aug. 12, 1980

[54] PRESERVATION OF AQUEOUS SYSTEMS WITH α-CHLORO-β-AMINOCROTONAMIDE

[75] Inventors: Harold A. Brandman, Glen Ridge; Milton Manowitz, Wayne; David L. Coffen, Glen Ridge, all of N.J.

[73] Assignees: Givaudan Corporation, Clifton; Hoffmann-La Roche Inc., Nutley, both of N.J.

[21] Appl. No.: 934,308

[22] Filed: Aug. 17, 1978

[51] Int. Cl.$^2$ .................... A01N 9/20; C07C 103/133; D21F 1/66
[52] U.S. Cl. ................... 424/320; 106/18.32; 106/18.35; 162/161; 252/8.75; 252/49.5; 260/561 A
[58] Field of Search .................... 260/561 A; 424/320

[56] References Cited

U.S. PATENT DOCUMENTS

| 4,025,651 | 5/1977 | Kirino et al. | 424/320 |
| 4,079,148 | 3/1978 | Oeckl et al. | 424/320 X |
| 4,093,654 | 6/1978 | Coffen | 260/561 A |

FOREIGN PATENT DOCUMENTS

| 4429479 | 1/1969 | Japan | 424/320 |
| 638662 | 6/1950 | United Kingdom | 424/320 |

*Primary Examiner*—Dale R. Ore
*Attorney, Agent, or Firm*—Robert F. Tavares; Thomas Cifelli, Jr.

[57] ABSTRACT

Methods and compositions for inhibiting or preventing the growth of microorganisms in aqueous systems wherein the growth is inhibited or prevented by the presence of an effective amount of α-chloro-β-aminocrotonamide.

9 Claims, No Drawings

PRESERVATION OF AQUEOUS SYSTEMS WITH α-CHLORO-β-AMINOCROTONAMIDE

A number of aqueous systems are susceptible to antimicrobial growth. Among these are cosmetics, latex paints, polymer emulsions and other oil water emulsions, cutting oils, adhesives, water used in industrial cooling towers, white water in the paper mills and the like. The growth of bacteria and fungi in such systems can be a serious problem if not properly controlled. For example, industrial aqueous systems are susceptible to slime formation which, if unchecked, can cause severe maintainance and production problems. Similarly, consumer products such as cosmetics can be damaged by the growth of bacteria, fungi or algae.

There is, consequently, a continuing need to provide effective and economical antimicrobial agents which protect these systems. The finding of this invention is that compositions and methods utilizing α-chloro-β-aminocrotonamide provide effective control of such microbial growth. The α-chloro-β-amino-crotonamide has been found effective against a broad spectrum of bacteria including gram positive bacteria, gram negative bacteria and fungi. The breadth of such activity is illustrated in the examples.

The α-chloro-β-aminocrotonamide is described in U.S. Pat. No. 4,093,654, but no mention is made regarding its antimicrobial properties.

DESCRIPTION OF THE PREFERRED EMBODIMENTS

The α-chloro-β-aminocrotonamide may be added to the aqueous systems or formulations undiluted or dissolved in organic solvents such as alcohols, acetone, dimethylformamide and the like. It may be added alone or in combination with other biocides and/or functional compounds such as antioxidants, anticorrosive agents, surfactants, etc.

Concentrations from about 0.001% to about 0.2% are effective. Use of larger concentrations, while feasible, is recommended only for unusual applications. It is preferred to use concentrations from about 0.005% to about 0.10%.

The α-chloro-β-aminocrotonamide can be used as a preservative for oil in water emulsions. A number of oil water emulsions are used in industry, for example in the high speed metal working and textile industries, for their cooling, lubricating, antistatic and anticorrosive properties. Unless adequately protected by an effective preservative, such systems are susceptible to bacterial decomposition producing obnoxious odors and potential health hazards. [Detailed descriptions of these systems, their microbiological problems and difficulties in their preservation can be found in: Bennet, E. O., Soap Chem. Specialties, 32, 46 (1956). Fabian, F. W. & Pivnick, H., Applied Microbiology, 1, (1953).]

In practicing the invention, the active ingredient may be added by directly dissolving it in the concentrated oil which is then diluted with water to form the water oil emulsion, or it may be added to the final emulsion either undiluted or dissolved in a solvent such as dimethylformamide, alcohol, acetone, etc. Similar methods known in the art for adding preservatives to such water and oil emulsions may also be used.

There can be used as little as about 0.005%. Although amounts greater than 0.3% are operable, they are recommended only for unusual applications. It is preferred to use amounts in the range of from about 0.01% to about 0.20%, with amounts in the range of about 0.02% to 0.10% being especially preferred.

The α-chloro-β-aminocrotonamide is particularly effective as a cosmetic preservative [Problems encountered in the preservation of cosmetics are described by Dunnigan, A. P., Drug and Cosmetic Industries, 103, 43, (1968)].

The compound may be added to the finished cosmetic product directly or dissolved in suitable solvents such as alcohol, acetone, dimethyl formamide and the like. Alternatively the compounds may be dissolved in the oils or other raw materials used in the formula and then formulated in the final product.

In cosmetic preparations, concentrations as low as 0.10% are found to be operable. Concentrations greater than 0.30%, while operable, are recommended only for unusual applications. Concentrations in the range of from about 0.02% to about 0.20% are preferred with concentrations of about 0.05% to 0.10% being especially preferred.

The α-chloro-β-aminocrotonamide is particularly effective as a slimicide. For example it can be used to protect so-called white water systems utilized in paper manufacture from the formation of slimes and the like which are known to affect these systems. Concentrations as low as 0.005% are found to be operable. Concentrations greater than 0.20%, while operable, are recommended only for unusual applications. Concentrations in the range of from about 0.007% to about 0.15% are preferred with concentrations of about 0.01% to about 0.10% being especially preferred.

While the compound is effective when added directly, it is preferred to add it dissolved in a suitable solvent such as diethylene glycol, dipropylene glycol or polyethylene glycol and the like. Other methods known in the art for adding preservatives to such aqueous systems may also be used.

ILLUSTRATION OF PREFERRED EMBODIMENTS

A number of examples are provided herein to illustrate the preferred embodiments of this invention. The examples provided are included for the sole purpose of illustrating the preferred embodiments and should not be construed as limiting. They are intended to embrace any equivalents or obvious extensions which are known or should be known to a person skilled in the art.

EXAMPLE I

The following illustrates the method of synthesis of the α-chloro-β-aminocrotonamide.

About 200 ml of ammonia were condensed in a 500 ml flask cooled in a dry ice/acetone bath. Diketene (84 g, 1 mol) was added dropwise with stirring. An additional 100 ml of liquid ammonia was added and the mixture was left overnight during which the excess ammonia was allowed to evaporate. The solid β-aminocrotonamide was removed from the flask and left in the air for two hours to allow residual ammonia to escape. It was then transferred to a 3l flask, dissolved in cold water (250 ml), and cooled to 10° with an ice/acetone bath. Aqueous sodium hypochlorite (5.25% solution, "Chlorox", 1500 ml, 1 mol) was added gradually with rapid mechanical stirring. The rate of addition was controlled so that the temperature of the reaction did not exceed 10°. When addition was completed, the product was collected, washed sparingly with cold water, and air-dried to give 80.3 g of colorless solid. Ether extraction of the aqueous filtrate afforded an additional 7.4 g of product giving a yield of 87.7 g (65.5%).

EXAMPLE II

General Antimicrobial Activity

The α-chloro-β-aminocrotonamide is active against wide variety of microorganisms as illustrated by the following test.

A 6% solution of α-chloro-β-aminocrotonamide in dimethyl formamide was prepared. The 6% solution was then 5-fold serially diluted in test tubes to give the desired concentrations when mixed with agar and poured into sterile Petri dishes. For instance, 0.8 ml of a 6% stock solution plus 24.2 ml of agar gives a test concentration of 1920 mcg/ml, the highest level tested. Tryptone glucose extract agar is used for the bacterial testing; mildew glucose agar for the fungal testing. The bacterial plates were spot inoculated with 24-hour nutrient broth cultures and incubated at 37° C. for 48hours. The fungal plates were spot inoculated with spore suspensions and incubated at 28° C. for seven days. At the end of the incubation periods, all plates were examined for growth. The minimum inhibitory concentration (MIC) for each organism is expressed in Table I. In the ranges presented, growth is observed only at the lower concentration.

TABLE I

| | Minimum Inhibitory Concentration Range |
|---|---|
| Bacteria | |
| Staphylococcus aureus | 15 μg/ml–76 μg/ml |
| Escherichia coli | 3 μg/ml–15 μg/ml |
| Pseudomonas aeruginosa | 15 μg/ml–76 μg/ml |
| Proteus vulgaris | 15 μg/ml–76 μg/ml |
| Bacillus subtilis | 76 μg/ml–384 μg/ml |
| Fungi | |
| Aspergillus niger | 15 μg/ml–76 μg/ml |
| Aspergillis oryzae | 76 μg/ml–384 μg/ml |
| Penicillium piscarium | 76 μg/ml–384 μg/ml |
| Aureobasidium pullulans | 15 μg/ml–76 μg/ml |

EXAMPLE III

Utility as a Cosmetic Preservative

The α-chloroβ-aminocrotonamide is an effective cosmetic preservative. Two-fold serial dilutions of 6% solutions of the α-chloroβ-aminocrotonmide in dimethylformamide were added to a cosmetic lotion of the following formulation:

| | |
|---|---|
| Stearic acid | 1.4 g |
| Mineral Oil | 2.3 g |
| Arlacel 60 (sorbitan monostearate) | 0.7 g |
| Tween 20 [Polyoxethylene (20) sorbitan monostearate] | 1.6 g |
| Distilled water | 94.0 g |

The lotions were inoculated with both *Pseudomonas aeruginosa* and *Aspergillus niger* and incubated at 28° C. At weekly intervals, the lotions were examined for microorganisms by conventional streak-plate methods or by macroscopic observation. The lotions were then reinoculated with the test organisms and reincubated.

Table II shows the minimum inhibitory concentration that was effective in preventing microbial growth for the four week period.

TABLE II

| | Minimum Inhibitory Concentration Range (micrograms/milliliter) | |
|---|---|---|
| Week | Pseudomonas aeruginosa | Aspergillus niger |
| 1 | <125 μg/ml | <125 μg/ml |
| 2 | <125 μg/ml | <125 μg/ml |
| 3 | <125 μg/ml | 125–250 μg/ml |
| 4 | <125 μg/ml | 500–1,000 μg/ml |

Tests run in other cosmetic formulations gave similar results.

EXAMPLE IV

The utility of the α-chloro-β-aminocrotonamide in water and oil emulsions is illustrated below using a commericially available cutting oil and a commericially available textile lubricant.

A. Utility as a Cutting Oil Preservative

The α-chloro-β-aminocrotonamide is an effective cutting oil preservative. The data of Table III clearly illustrate its effectiveness.

In running these tests, two-fold serial dilutions of 6% solutions of the compound in dimethylformamide was added to 3.3% cutting oil emulsions. The emulsions were prepared by diluting with water a commercially available cutting oil concentrate. The emulsions were inoculated with a culture of *Pseudomonas aeruginosa* and incubated at 28° C. on a rotary shaker. At weekly intervals, the emulsions were examined for bacteria by conventional streak-plate methods. The emulsions were then reinoculated with *Pseudomonas aeruginosa* and reincubated.

TABLE III-A

| Week | Minimum Inhibitory Concentration Range (micrograms/milliliter) Pseudomonas aeruginosa |
|---|---|
| 1 | <31.3 μg/ml |
| 2 | 250–500 μg/ml |
| 3 | 500–1,000 μg/ml |
| 4 | 500–1,000 μg/ml |

B. Utility as a Textile Lubricant Preservative

The test run was the same as for the cutting oil above except that a commercial textile lubricant was substituted for the cutting oil.

TABLE III-B

| Week | Minimum Inhibitory Concentration Range (micrograms/milliliter) Pseudomonas aeruginosa |
|---|---|
| 1 | <31.3 μg/ml |
| 2 | 31.3–62.5 μg/ml |
| 3 | 125–250 μg/ml |
| 4 | 250–500 μg/ml |

EXAMPLE V

The utility of the α-chloro-β-aminocrotonamide as a slimicide for pulp and paper mill water systems was demonstrated by the following study.

Various quantities of a 6% solution of this compound in dimethylformamide were incorporated into 24 ml of a test substrate composed as follows:

8.4 g: Whatman No. 2 powdered cellulose
2.6 g: Sodium nitrate
1.0 g: Calcium sulfate
6.5 g: Maltose
1.0 g: Nutrient Broth, Difco
10.0 ml: Mersize Rm 70R (Monsanto)
2.5 ml: 2% Alum
990 ml: Distilled water The samples were inoculated with four different organisms and incubated at 28° C. At weekly intervals the samples were examined for the presence of microbial growth and reinoculated during a total incubation period of four weeks. The results as tabulated in Table IV show that α-chloro-β-aminocrotonamide is effective as a slimicide at a concentration of 0.0125%-0.0250%.

TABLE IV

Effectiveness of α-Chloro-β-aminocrotonamide as a Slimicide (mcg/ml)

| Organism | Weeks | | | |
|---|---|---|---|---|
| | 1 | 2 | 3 | 4 |
| P. aeruginosa | 15.6–31.3 | 15.6–31.3 | 15.6–31.3 | 15.6–31.3 |
| E. aerogenes | 62.5–125 | 125–250 | 125–250 | 125–250 |
| A. Niger | 31.3–62.5 | 62.5–125 | 125–250 | 125–250 |
| P. piscarium | 125–250 | 125–250 | 125–250 | 125–250 |

We claim:

1. A method of inhibiting or preventing the growth of bacteria and fungi in an aqueous composition subject to spoilage thereby which comprises incorporating in said composition an effective amount of α-chloro-β-aminocrotonamide.

2. A method according to claim 1 wherein the α-chloro-β-aminocrotonamide is utilized at a level of from about 0.01% to about 0.2%.

3. A method according to claim 2 wherein there is utilized from about 0.02 to about 0.1%.

4. The method of claim 1 wherein the composition to be protected is a cosmetic formulation.

5. The method of claim 1 wherein the composition to be protected is a water and oil emulsion.

6. The method of claim 1 wherein the composition to be protected is a white water system used in paper manufacture.

7. A cosmetic composition comprising an amount of α-chloro-β-aminocrotonamide effective to inhibit or prevent the growth of bacteria and fungi.

8. An oil and water emulsion comprising an amount of α-chloro-β-aminocrotonamide effective to inhibit or prevent the growth of bacteria and fungi.

9. A white water system used in paper manufacture comprising an amount of α-chloro-β-aminocrotonamide effective to inhibit or prevent the growth of bacteria and fungi.

* * * * *